United States Patent [19]

Huber

[11] 4,042,338
[45] Aug. 16, 1977

[54] AUTOMATIC SAMPLE PREPARATION DEVICE

[75] Inventor: Bernhard Werner Huber, Uberlingen, Germany

[73] Assignee: Bodenseewerk Perkin-Elmer & Co. GmbH, Uberlingen, Germany

[21] Appl. No.: 710,015

[22] Filed: July 30, 1976

[30] Foreign Application Priority Data

Sept. 13, 1975 Germany .............................. 2540969

[51] Int. Cl.² .............................................. G01N 1/14
[52] U.S. Cl. .................................. 23/259; 23/253 R; 73/425.4 P; 73/425.6; 141/130
[58] Field of Search ................. 23/259, 253 R, 230 R; 73/425.4 R, 425.4 P, 425.6; 141/130

[56] References Cited

U.S. PATENT DOCUMENTS

| 3,475,130 | 10/1969 | Baruch | 23/259 |
|---|---|---|---|
| 3,728,079 | 4/1973 | Moran | 23/259 X |
| 3,912,456 | 10/1975 | Young | 23/253 R |
| 3,917,455 | 11/1975 | Bak et al. | 23/253 R |

Primary Examiner—R.E. Serwin
Attorney, Agent, or Firm—S. A. Giarratana; F. L. Masselle; E. T. Grimes

[57] ABSTRACT

An automatic sample preparation device for use in flameless atomic absorption spectroscopy or the like, wherein samples to be examined for a particular element are successively mixed with graduated, metered additions of the element to be determined, which includes, in combination, controlled delivery pumping apparatus, a storage vessel system containing dilution agents connected to the inlet side of the pumping apparatus, a dosing probe connected to the outlet side of the pumping apparatus, a stepwise movable carrier, a plurality of sample containers mounted on the carrier, a sample withdrawing device for withdrawing samples from the carrier, and a control unit for moving the dosing probe with respect to the carrier so that one group of at least two successive sample containers on the carrier can be simultaneously mixed with graduated, metered additions of the element to be determined prior to sample withdrawal.

18 Claims, 4 Drawing Figures

AUTOMATIC SAMPLE PREPARATION DEVICE

BACKGROUND OF THE INVENTION

This invention is directed to an automatic sample preparation device, and more particularly to such a device for use with flameless atomic absorption spectroscopy, such as, for example, one where the samples which are to be analyzed one after the other for a definite element, are provided with stepped, metered additions of the element to be analyzed.

It will be appreciated that, in spectroscopic analysis of samples of different origins for specific components, errors of the measured values may be caused by additions, depending on the origin of the sample. This prevents a calibration curve, established for the analytical determination of a given component in a sample obtained from a specific origin, from being transferred to a sample from another origin. The problems occurring in such cases were normally overcome by the addition to the sample of known quantities of the component to be analyzed, and by extrapolating from the values thus obtained to the contents of the element concerned in the sample at zero addition. See, for example, the publication entitled, "Analysentechnische Berichte", No. 32, (1974), page 10. Further, U.S. Pat. No. 3,764,268 issued Oct. 9, 1973 contains disclosure related to this art.

However, the above procedure was very time-consuming and inconvenient when a great number of samples had to be handled. The purpose of this invention consists in providing a device for automating this procedure.

SUMMARY OF THE INVENTION

In order to accomplish the desired results, this invention provides a new and improved automatic sample preparation device for use in flameless atomic absorption spectroscopy of the like, wherein samples to be examined for a particular element are successively mixed with graduated, metered additions of the element to be determined. The device includes, in combination, controlled delivery pump means, storage vessel means containing dilution agents connected to the inlet side of the delivery pump means and a dosing probe connected to the outlet side thereof. A stepwise movable carrier is provided for carrying a plurality of sample containers thereon, and a sample withdrawing device serves to withdraw samples from the sample containers. A control unit is provided for moving the dosing probe with respect to the carrier so that one group of at least two successive sample containers on the carrier can be simultaneously mixed with graduated, metered additions of the element to be determined prior to sample withdrawal.

In one form of the invention, the storage vessel means comprises a first storage vessel containing pure solvent, and at least one and preferably two additional storage vessels containing a predetermined concentration of the element to be determined in the solvent. According to an aspect thereof, the controlled delivery pump means comprises one delivery pump for each storage vessel and a dosing probe for each delivery pump.

According to a form of the invention, the delivery pumps are pipet pumps mounted on a movable support frame, and means are provided for moving the support frame from a first position wherein the pipet pumps aspirate a metered quantity of diluting agent from the storage vessels, respectively, to a second position wherein the pipet pumps add the diluting agent to the sample containers, respectively.

In another form of the invention, the delivery pumps are flow type pumps, which are fixedly mounted, and means are provided for jointly moving the dosing probes from a first position above the containers, respectively, to a second position wherein the probes are inserted in the sample containers above the liquid level therein, respectively.

In still another form of the invention, the delivery pumps are diluter type pumps, which are fixedly mounted, and means are provided for jointly moving the dosing probes from a first position wherein they are jointly dipped into a sample storage vessel to a second position, after having aspirated a metered quantity of the sample, wherein they are disposed above the sample containers, respectively. Further, the device includes means for jointly moving the dosing probes to another position wherein they are arranged inside the sample containers above the liquid level, respectively.

The invention, in another form thereof, is characterized by the controlled delivery pump means being in the form of a multiple pump having a plurality of delivery units and a common drive unit.

According to an aspect of the invention, only one additional storage vessel is provided, which contains a predetermined concentration of the element to be determined in the solvent. The controlled delivery pump means comprises a single delivery pump, which is a diluter type pump, that is fixedly mounted. In addition, means are provided for graduating the mixing ratio of solvent and solution in the diluant that is fed to the individual sample containers within the particular group of sample containers. The device includes means for moving the dosing probe from a first position wherein it is dipped into a sample storage vessel, to a second position, after having aspirated a metered sample quantity, wherein it is disposed above one of the group of successive sample containers in the carrier means. The device further includes means for setting differently the mixing ratio between the pure solvent and the solution of the element to be determined for each sample container of the group.

According to still another aspect of the invention, a drive unit is provided for the pumping means, which is connected in a power supply circuit containing a switch that is controlled by the carrier means. The carrier means is characterized by being in the form of a turntable, and a plurality of spaced switching cams are mounted toward the periphery thereof for actuating the switch, the distance between the switching cams being determined by the number of sample containers forming one group.

In one other form of the invention, the storage vessel means comprises a single storage vessel, and the delivery pump means comprises a single pipet pump. The sample withdrawing device is arranged to withdraw a plurality of samples from a single sample container, and the pipet pump adds to said sample container a metered quantity of dilution agent before each sample withdrawal, and the carrier is movable one step after completing said plurality of withdrawals.

There has been thus outlined rather broadly the more important features of the invention in order that the detailed description thereof that follows may be better understood, and in order that the present contribution to the art may be better appreciated. There are, of course, additional features of the invention that will be described hereinafter and which will form the subject of the claims appended hereto. Those skilled in the art will appreciate that the conception upon which the disclosure is based may readily be utilized as a basis for the designing of other structures for carrying out the several purposes of the invention. It is important, therefore, that the claims be regarded as including such equivalent structures as do not depart from the spirit and scope of the invention.

Specific embodiments of the invention have been chosen for purposes of illustration and description, and are shown in the accompanying drawings, forming a part of the specification.

BRIEF DESCRIPTION OF THE DRAWINGS

It is noted that, for purposes of simplification, corresponding parts are designated by the same reference numerals in the various figures.

Figure 1:
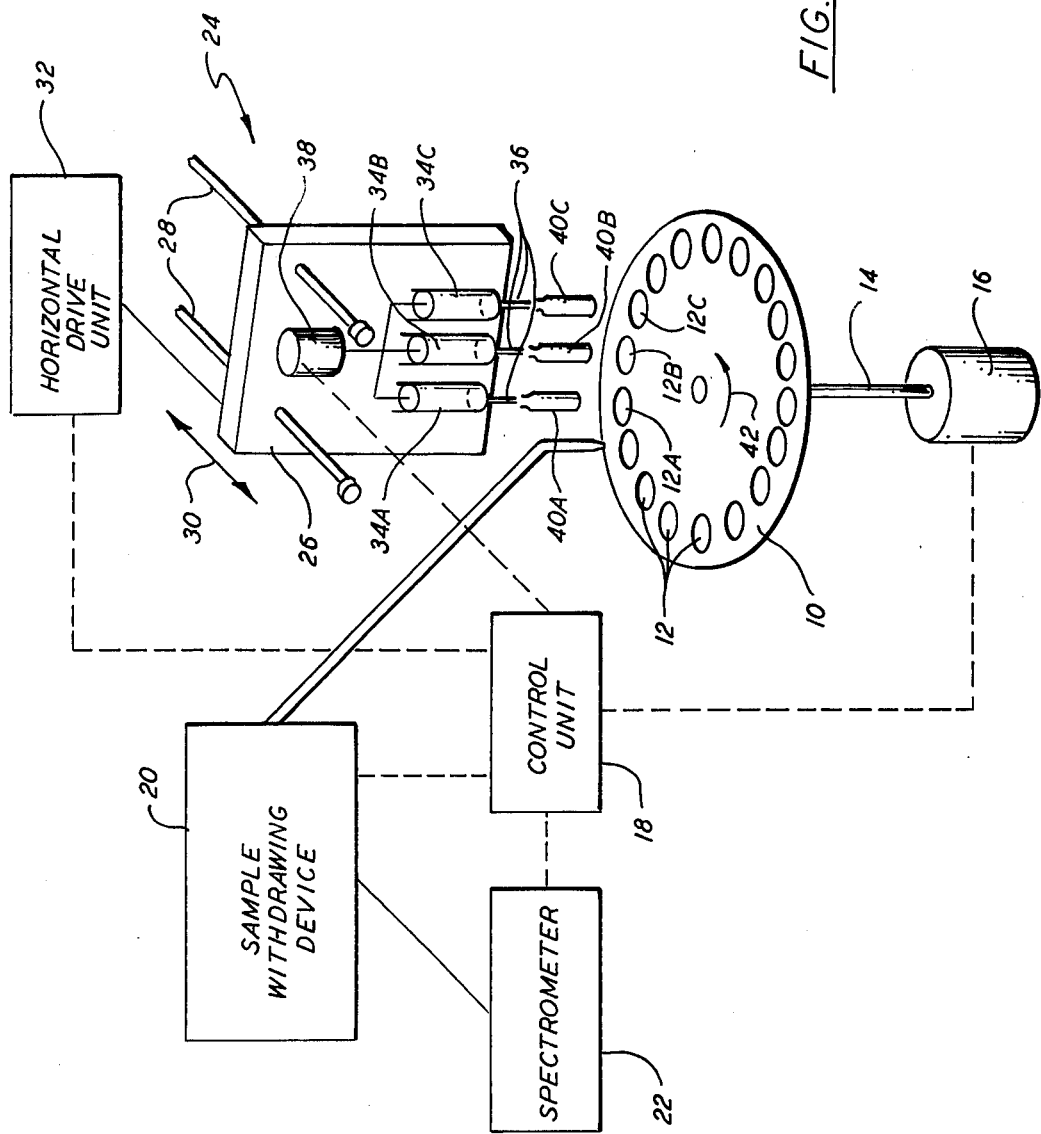
FIG. 1 is a schematic representation of a first embodiment of the sample preparation device according to the invention, using pipet type pumps.
Figure 2:
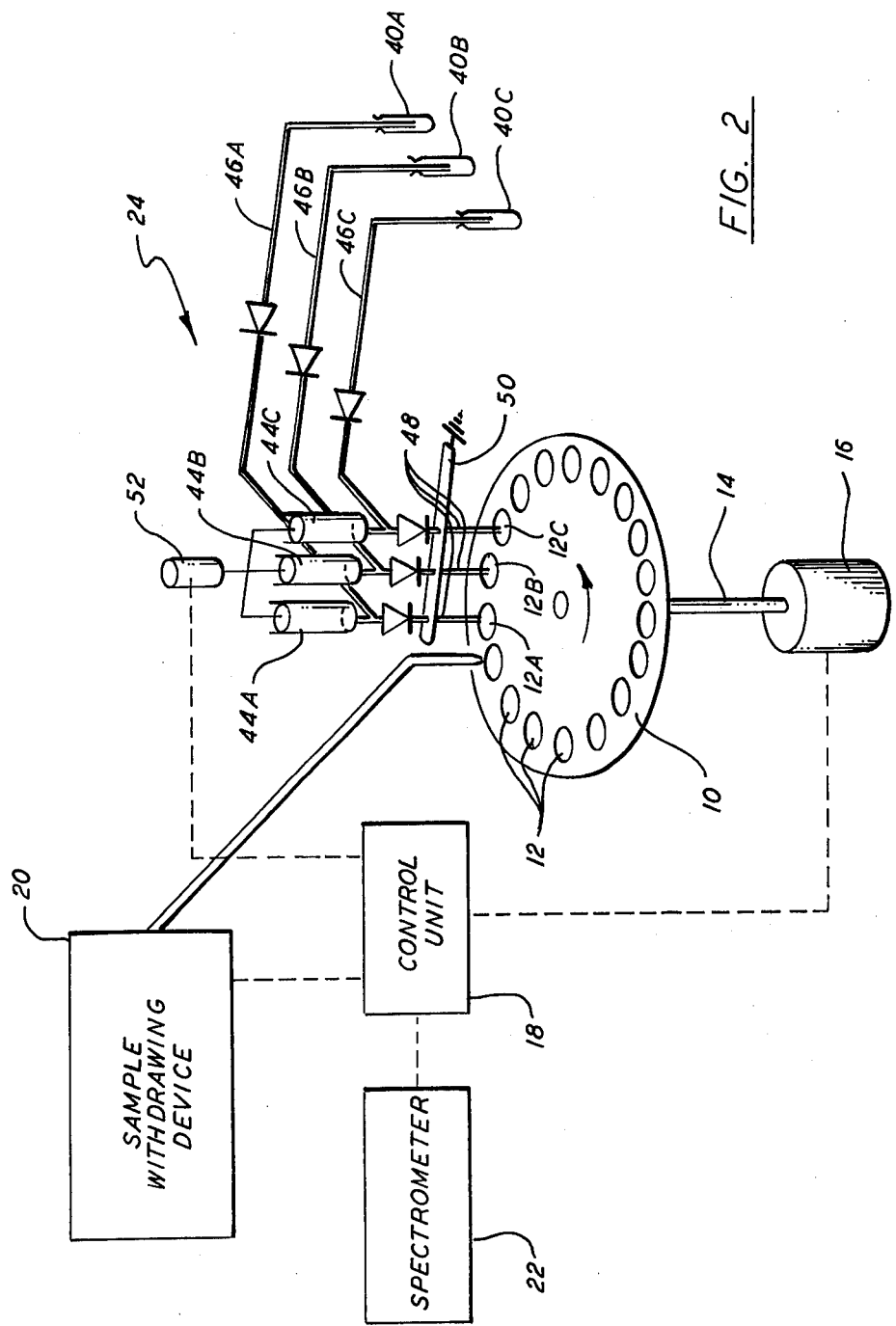
FIG. 2 is a schematic representation similar to FIG. 1, but showing another embodiment of the invention, using flow type pumps.
Figure 3:
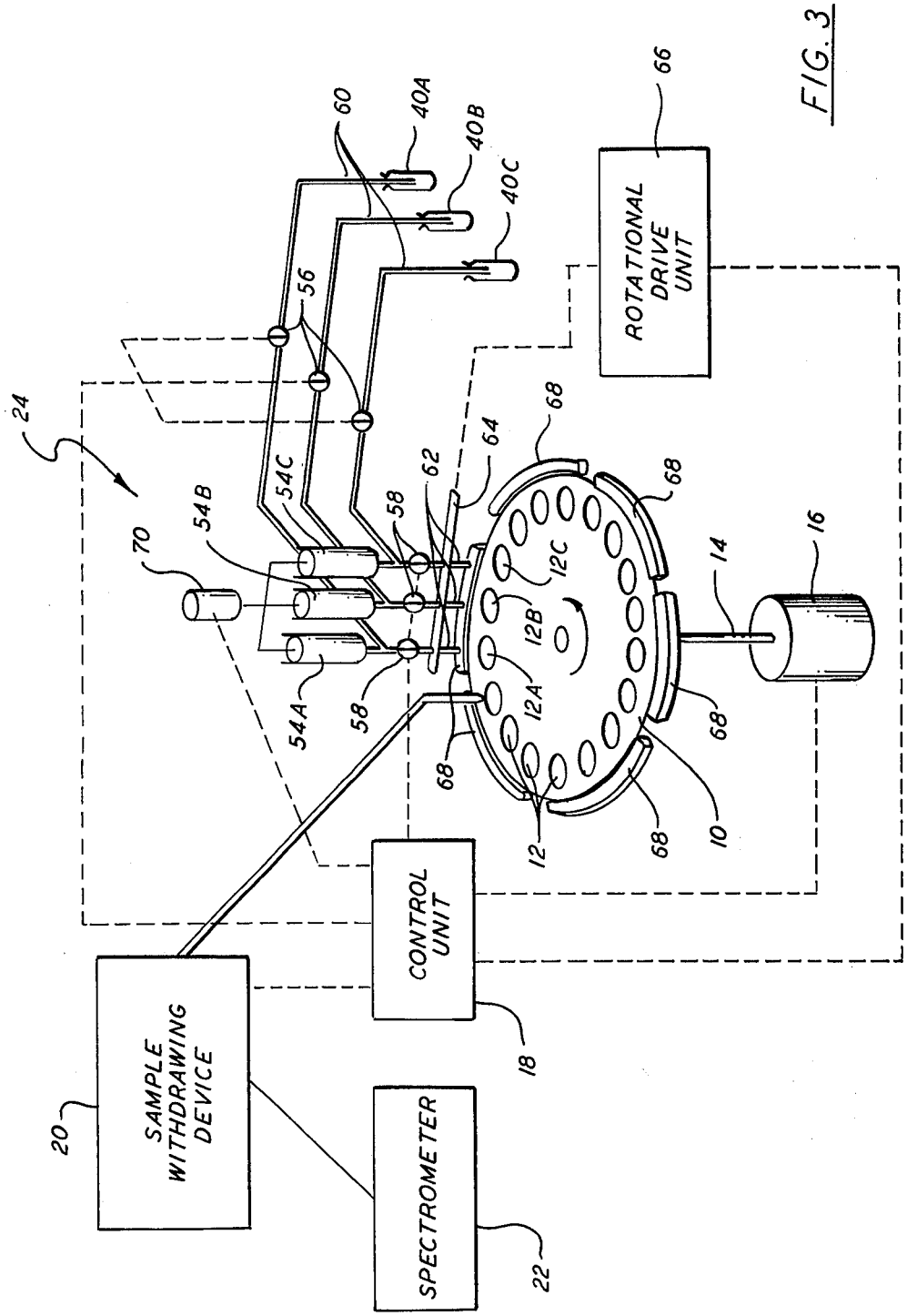
FIG. 3 is a schematic representation similar to FIGS. 1 and 2, but showing still another embodiment of the invention, using diluter type pumps.

In the embodiments of the invention illustrated in FIGS. 1 to 3, the automatic sampling preparation device includes a turntable 10 that is adapted for receiving a plurality of sample containers 12 mounted around the periphery thereof in spaced relationship. The turntable is rotatable in step-wise fashion to bring each container into operative position by means of a drive shaft 14 and motor 16, the motor being controlled by a master control unit 18 in order to synchronize the various operations of the device. Mounted adjacent the turntable 10 is a sample withdrawing device 20, which is adapted to withdraw samples from one or more of the sample containers 12 for analysis in a flameless atomic absorption spectrometer having heated graphite atomizer, indicated at 22.

In the embodiment of the device illustrated in FIG. 1, the automatic sampling preparation device further includes a delivery pump assembly, indicated generally at 24, for adding to the sample, metered quantities of the element to be tested for. This assembly includes a support frame 26 mounted for reciprocating horizontal movement on support bars 28, as indicated by the arrow 30, by means of a horizontal drive unit 32. At least one and preferably three pipet type pumps 34A, 34B and 34C, each having a dosing probe 36, are mounted on the support frame 26 for vertical reciprocating motion. A single drive unit 38 serves to activate the pumps, but it will be appreciated that a separate drive unit could be provided for each pump. A like number of storage vessels, preferably three, 40A, 40B and 40C, are disposed adjacent the turntable 10, the first vessel 40A containing a solvent, e.g. water; the second vessel 40B containing a preselected concentration of the element to be analyzed in a water solution; and the third vessel 40C containing a higher concentration such as, for example, twice the concentration of that of the second vessel, of the element to be analyzed in a water solution.

In operation, the control unit 18 directs drive unit 38 to move the pipet pumps 34A, 34B and 34C downwardly until the dosing probes 36 are immersed in the liquid contained in the storage vessels 40A, 40B and 40C, respectively. The pipet pumps are then operated so as to aspirate a metered liquid volumn from the storage vessels. Thereafter, the control unit 18 directs the horizontal drive unit 32 to move the support frame 26 to a second position wherein the dosing probes 36 are positioned over the sample containers 12A, 12B and 12C. Next, the dosing probes are moved downwardly into the sample containers 12A, 12B and 12C. respectively, but above the liquid level in these containers by means of the drive unit 38. During the next step, the liquid contained in the pipet pumps 34A, 34B and 34C is dispensed and thus introduced into the sample containers. When this operation has been completed, the dosing probes are withdrawn, and the support frame 26 is returned to its original position. The control unit 18 instructs the motor 16 to index the turntable 10 one step in the direction of arrow 42 so that the prepared samples can be withdrawn by the sample withdrawing device 20 from the sample container, for analysis in the spectrometer 22. The turntable, under the control of the control unit 18, is indexed until the three prepared samples have been analyzed and the device is ready to repeat the aforesaid series of operations.

It will be appreciated that in the arrangement of FIG. 1, each pipet pump is correlated to a specific storage vessel and, consequently, no flushing processes are required between the individual operating steps. In the illustrated embodiment, the group of sample containers to be successively analyzed consists of three sample containers and, hence, for instance, if the lead content of a liquid sample is to be determined, equal metered sample quantities are introduced into the sample containers 12A, 12B, and 12C. This is effected prior to the operation of the sample preparation device. With this arrangement, a metered quantity of water is then introduced into sample container 12A; and equal quantity of a solution containing 0.25 p.p.m. lead is introduced into sample container 12B; and an equal metered quantity of a solution containing 0.5 p.p.m. is introduced into sample container 12C. Next, individual samples are withdrawn from this group of sample containers, and the lead content of these samples is determined in the spectrometer 22. The lead content of the samples can be determined from extrpolation to lead addition zero, while taking simultaneously into consideration the dilution.

According to one aspect of the invention the device described hereinbefore in connection with FIG. 1 may be modified. In this form of the invention, only one storage vessel 40A and only one pipet pump 34A are employed, and the pump is mounted for movement on the support frame 26 in the described manner. The storage vessel 40A contains a known concentration of the element to be determined in solution, and the sample container 12A on the turntable contains from double to ten times the quantity of the sample that is to be tested. In operation, the turntable 10 is stepped until the sample container 12A is moved to its operative position, wherein the sample withdrawing device 20 withdraws a sample from the sample container and passes it to the spectrometer 22. Subsequently, the pipet pump aspirates a preselected quantity of solution from the storage vessel 40A and adds it to the sample container 12A. Then the sample withdrawing device withdraws a second sample from the same sample container for analysis in the sectrometer. At the same time the pipet pump 34A aspirates a third preselected quantity of solution from the storage vessel 40A and adds it to the sample container 12A, which is, in turn, withdrawn and analyzed. This process can be repeated as many times as is necessary for the analysis. It is noted that in this form of the invention, the turntable is stepped only after the withdrawal of the last sample from the sample container 12A.

In the embodiment of the invention illustrated in FIG. 2, the turntable 10, sample containers 12, drive motor 16, control unit 18, sample withdrawing device 20 and spectrometer 22 employed are the same as those employed in the embodiment of FIG. 1. In the delivery pump assembly 24, the pipet type pumps 34A, 34B and 34C of FIG. 1 have been replaced by flow type pumps 44A, 44B and 44C, which are mounted in a stationary manner. While three flow pumps are illustrated, the system may be operated with less than or more than three pumps, as will be described more fully hereinafter. The inlets of these pumps are connected via connecting lines 46A, 46B and 46C to the storage vessels 40A, 40B and 40C, respectively. The storage vessels contain the same constituents as indicated hereinbefore in connection with the embodiment of FIG. 1. However, in this embodiment the storage vessels may be located at a distance from the turntable, if desired. Each of the outlets of the flow pumps is connected to a dosing probe 48. The dosing probes are flexibly connected to their respective pump outlets and are mounted on a support member 50 for vertical movement, with a drive device 51 being provided for activating the flow pumps and vertically positioning the dosing probes. While a single drive unit is illustrated, separate drive units could be provided for each pump, if desired, for a particular installation. Thus, the dosing probes 48 are movable from their positions seen in FIG. 2 to their lower positions, wherein each probe is immersed in a correlated sample container just above the liquid level therein. In operation, the dosing probes 48 are retained in their upper positions during the time when the turntable is being indexed and are retained in their lower positions during the time when the liquid quantities withdrawn from the storage vessels are being added to the sample containers.

FIG. 3 shows another embodiment of the invention wherein the turntable 10, sample containers 12, drive motor 16, control unit 18, sample withdrawing device 20 and spectrometer employed are the same as those employed in the embodiment of FIGS. 1 and 2. In this embodiment, the delivery pump assembly 24 employs diluter type pumps 54A, 54B and 54C instead of the flow pumps 44A, 44B and 44C used in the embodiment of FIG. 2. These diluter pumps differ from the flow pumps by virtue of the use of control valves 56 and 58. That is, the inlets of the diluter pumps 54A, 54B and 54C are connected to the solvent storage vessels 40A, 40B and 40C, respectively, through connecting lines 60 containing control valves 56 that are actuated by the master control unit 18. As indicated in the description of the embodiment of FIG. 1, the first of the storage vessels 40A contains solvent; the second vessel 40B contains a preselected concentration of the element to be analyzed; and the third vessel 40C contains a higher concentration of the element being analyzed. Sampling probes 62 are connected to the outlets of the diluter pumps 54A, 54B and 54C through outlet control valves 58 that are actuated by the master control unit 18. The sampling probes 62 are jointly movably mounted on a support member 64 by means of a rotational drive unit 66 so that in one position thereof they dip into a sample contained in a sample storage vessel 68 mounted on the turntable 10 and in another position thereof they dip into the sample containers 12, as will be described more fully hereinafter.

In operation, when the device is in its position as shown in FIG. 3, the valves 56 are closed and the valves 58 are opened, as instructed by the control unit 18. The diluter pumps 54A, 54B and 54C are actuated by a drive unit 70 controlled by the control unit 18 to aspirate a metered sample quantity from the sample storage vessel 68 through the probes 62. Then the valves 58 are closed and the valves 56 are opened. Now, the diluter pumps aspirate a metered quantity of the particular solution from the storage vessels 40A, 40B and 40C. After completing this step, the valves 56 are closed and the sampling probes 62 are raised to a first upper position, where they are on a plane above the sample storage vessel 68 and the turntable 10. Thereafter, the sampling probes 62 are jointly rotated about an axis of the support member 64 by the drive unit 66 to a second upper position, where each probe is arranged above a sample vessel 12A, 12B and 12C. Next, the sampling probes on the support member 64 are moved downwardly to a second lower position where they dip into the sample containers to a level just above the liquid level in these containers. At this time the diluter pumps are actuated so that the sample quantities aspirated in the first lower position of the sampling probes are transferred into the sample containers and simultaneously the pure solvent is transferred into the sample container 12A, while at the same time known quantities of the element to be analyzed are transferred into the sample containers 12B and 12C.

It will be appreciated that one of the advantages of the embodiment of FIG. 3 results from the technical characteristics of diluter pumps. With this type of pump the ratio between the quantity of delivered pure solvent and the delivered quantity of the solution at constant total delivery is variable. It is, therefore, sufficient according to one aspect of the invention to provide only a single diluter pump 54A and only a first storage vessel 40A with pure solvent and only a second storage vessel 40B with a solution of known concentration of the element to be analyzed. Then, during the passage from one sample container to the other, the ratio of the quantities delivered from the first and second storage vessel is set differently, as required.

Figure 4:
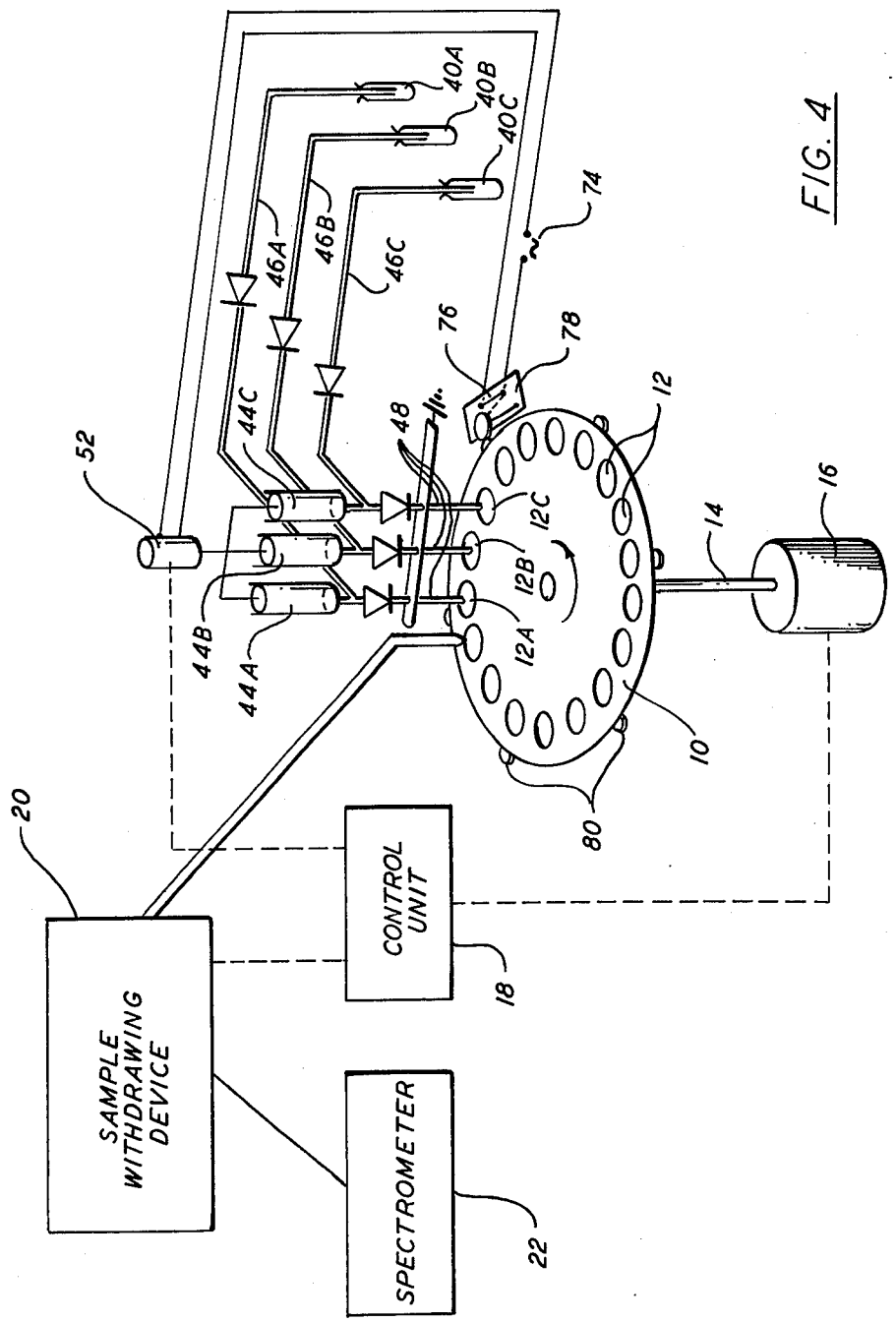
FIG. 4 is a schematic representation of a control system for the sample preparation device according to the invention.

Referring next to the embodiment of the invention illustrated in FIG. 4, there is illustrated a control device for the sample preparation device. While this control device is described in connection with the embodiment of FIG. 2, it will be appreciated that is is equally applicable to the embodiments of FIGS. 1 and 3. This control device includes the drive device 52, which serves for activating the flow pumps 44A, 44B and 44C and for vertically moving the sampling probes 48. This drive device 52 is connected to a power source 74 via a circuit 75 containing a switch 76. The switch 76 has an activating member 78, that is disposed adjacent the outer rim of the turntable 10, and the turntable has mounted thereon switching cams 80 which are disposed towards the periphery thereof in spaced relationship to engage the activating member 78 for closing the switch 76. These cams are arranged so that one cam engages the activating member of the switch after one group of three sample containers have been indexed to the sample withdrawing device. In operation, when the last sample container of a group is in its withdrawal position adjacent the withdrawing device 20, the activating member 78 of the switch 76 is activated by the switching cam 80 so that the switch closes the power circuit for the drive device 52, whereby the preselected quantities of liquid are withdrawn from the storage vessel and added to the sample containers of the next following group.

It will be appreciated that the sample preparation devices illustrated in FIGS. 1 to 3 can also be equipped with delivery pumps of other known types, and that a group of sample containers may include more or less than three, depending on the analytical requirements. Further, instead of individual pumps, a single larger pump may be employed, which has the advantage of easier controllability of the pump activity.

It is noted that every measured value determined by means of the above described devices has been modified by the dilution steps made prior to the measurement, and therefore, requires a conversion to the desired concentration units. This conversion can be effected in a measuring value processing device which is appropriately programmed. A storage, display and/or printout device may be employed for displaying or printing the desired values.

Thus, an improved automatic sample preparation device has been shown. Although specific embodiments have been illustrated and described, it will be obvious to those skilled in the art that various modifications may be made without departing from the spirit of the invention, which is intended to be limited solely by the appended claims.

What is claimed is:

1. An automatic sample preparation device for use in flameless atomic absorption spectroscopy or the like, wherein samples to be examined for a particular element are successively mixed with graduated, metered additions of the element to be determined, comprising, in combination:
   controlled delivery pump means,
   storage vessel means containing dilution agents connected to the inlet side of said delivery pump means,
   a plurality of dosing probes connected to the outlet side of said delivery pump means,
   stepwise movable carrier means,
   a plurality of sample containers mountable on said carrier means,
   a sample withdrawing device for withdrawing samples from said sample containers,
   means for jointly moving said dosing probes with respect to said carrier means so that one group of at least two successive sample containers on said carrier means can be simultaneously mixed with graduated, metered additions of the element to be determined prior to sample withdrawal.

2. An automatic sample preparation device according to claim 1 wherein said storage vessel means comprises a first storage vessel containing pure solvent, and at least one additional storage vessel containing a predetermined concentration of the element to be determined in said solvent.

3. An automatic sample preparation device according to claim 2 wherein said controlled delivery pump means comprises one delivery pump provided for each storage vessel, and wherein a dosing probe is provided for each delivery pump.

4. An automatic sample preparation device according to claim 3 wherein said delivery pumps are pipet pumps.

5. An automatic sample preparation device according to claim 4 wherein said means for jointly moving said dosing probes with respect to said carrier means comprises a movable support frame, said pipet pumps being mounted on said support frame, and means for moving said support frame from a first position wherein said pipet pumps aspirate a metered quantity of diluting agent from said storage vessels, respectively, to a second position wherein said pipet pumps add said diluting agent to said sample containers, respectively.

6. An automatic sample preparation device according to claim 3 wherein said delivery pumps are flow pumps, and wherein the dosing probes are arranged above the sample containers, respectively.

7. An automatic sample preparation device according to claim 6 wherein said flow pumps are fixedly mounted, and said means for jointly moving said dosing probes with respect to said carrier means comprises means for jointly moving said dosing probes from a first position above said containers, respectively, to a second position wherein said probes are inserted in said sample containers above the liquid level therein, respectively.

8. An automatic sample preparation device according to claim 3 wherein said delivery pumps are diluter pumps for delivery of the metered quanitites of the diluent.

9. An automatic sample preparation device according to claim 8 wherein said diluter pumps are fixedly mounted, and said means for jointly moving said dosing probes with respect to said carrier means comprises means for jointly moving said dosing probes from a first position above the sample containers respectively to a second position wherein they are arranged inside the sample containers above the liquid level, respectively.

10. An automatic sample preparation device according to claim 8 wherein said diluter pumps are fixedly mounted, and said means for jointly moving said dosing probes with respect to said carrier means comprises means for jointly moving said dosing probes from a first position wherein they are jointly dipped into a sample storage vessel for aspirating a metered sample quantity, to a second position wherein they are disposed above the sample containers, respectively.

11. An automatic sample preparation device according to claim 1 wherein said controlled delivery pump means is a multiple pump having a plurality of delivery units and a common drive unit.

12. An automatic sample preparation device according to claim 2 wherein there is only one additional storage vessel containing a predetermined concentration of the element to be determined in said solvent, and wherein said controlled delivery pump means comprises a single delivery pump.

13. An automatic sample preparation device for use in flameless atomic absorption spectroscopy or the like, wherein samples to be examined for a particular element are successively mixed with graduated, metered additions of the element to be determined, comprising, in combination:
   a diluter pump,
   a first storage vessel containing substantially pure solvent, and one additional storage vessel containing a predetermined concentration of the element to be determined in said solvent, said storage vessels being connected to the inlet side of said diluter pump, a dosing probe connected to the outlet side of said diluter pump, stepwise movable carrier means, a plurality of sample containers mountable on said carrier means, means for moving said dosing probe into and out of said sample containers, sample withdrawing device for withdrawing samples from said sample containers, and means for graduating the mixing ratio of solvent and solution in the diluent that is fed to individual sample containers within a particular group of sample containers so that at least two successive sample containers on said carrier means can be mixed with graduated, metered additions of the element to be determined prior to sample withdrawal.

14. An automatic sample preparation device according to claim 13 wherein said diluter pump is fixedly mounted, and wherein said device further comprises means for moving said dosing probe from a first position wherein it is dipped into a sample storage vessel for aspirating a metered sample quantity, to a second position wherein it is disposed above one of the group of successive sample containers in the carrier means, and wherein said device further comprises means for setting differently the mixing ratio between the pure solvent and the solution of the element to be determined for each sample container of said group.

15. An automatic sample preparation device according to claim 1 further comprising a drive unit for said pump means, a power supply circuit for said drive unit, a switch mounted in said power supply circuit, which is actuated by the movement of said carrier means.

16. An automatic sample preparation device according to claim 15 wherein said carrier means is a turntable, and wherein said device further comprises a plurality of spaced switching cams mounted toward the periphery of said turntable for actuating said switch, the distance between said switching cams being determined by the number of sample containers forming said group.

17. An automatic sample preparation device for use in flameless atomic absorption spectroscopy or the like, wherein samples to be examined for a particular element are successively mixed with graduated, metered additions of the element to be determined, comprising, in combination:

a controlled delivery pump, a storage vessel containing a diluting agent connected to the inlet side of said delivery pump, a dosing probe connected to the outlet side of said delivery pump, stepwise movable carrier means, a plurality of sample containers mountable on said carrier means, means for moving said dosing probe into and out of said sample containers, a sample withdrawing device for withdrawing a plurality of samples from a single sample container, means for controlling said delivery pump for adding to said sample container a metered quantity of diluting agent before each sample withdrawal, and means for moving said carrier one step after completing said plurality of withdrawals.

18. An automatic sample preparation device according to claim 17 wherein said controlled delivery pump is a pipet pump.

* * * * *